United States Patent [19]
Hayenga et al.

[11] Patent Number: 4,935,369
[45] Date of Patent: Jun. 19, 1990

[54] ISOLATION OF ACTIVE MICROBIALLY PRODUCED BOVINE RENNIN

[75] Inventors: Kirk J. Hayenga, San Bruno; Virgil B. Lawlis, Pacifica, both of Calif.

[73] Assignee: Genentech, Inc., South San Francisco, Calif.

[21] Appl. No.: 26,422

[22] Filed: Mar. 16, 1987

Related U.S. Application Data

[63] Continuation of Ser. No. 452,251, Dec. 22, 1982, abandoned.

[51] Int. Cl.$^5$ .......................... C12N 9/64; C07K 3/12
[52] U.S. Cl. ...................................... 435/226; 435/816; 530/412
[58] Field of Search ...................... 435/172.3, 226, 212, 435/816, 68; 530/412, 415, 408, 422, 423

[56] References Cited

U.S. PATENT DOCUMENTS

3,661,594  5/1972  Imai et al. ............................ 435/226
4,666,847  5/1987  Alford et al. ........................ 435/253

OTHER PUBLICATIONS

Wetzel, R. et al, *Gene*, vol. 16, pp. 63–71, Dec., 1981.
Williams et al, *Science*, vol. 215, pp. 687–689, 1982.
Freedman, R. B. et al, *The Enzymology of Post-Translational Modification of Proteins*, vol. 1, pp. 166–170, 1980.
Orsini, G. et al, *J. Biol. Chemistry*, vol. 253, pp. 3453–3458, 1978.
*Merck Index* 10th Ed., pp. 1173–1174, 1983 The condensed Chem. Dictionary, 10th Ed, (rev. by Hawley), p. 889, 1981.
Foltmann et al, *J. Biol. Chem.*, vol. 254, pp. 8447–8456, 1979.
Lehninger, *Principles of Biochemistry*, pp. 177–179, Worth Publishers, 1982.
Marston, F. *Biochem. J.*, vol. 240, pp. 1–12, 1986.
Krueger, J. et al, Bio Pharm, pp. 41–45, 1989.

*Primary Examiner*—Elizabeth C. Weimar
*Assistant Examiner*—Marian C. Knode
*Attorney, Agent, or Firm*—James G. Passé

[57] ABSTRACT

This invention relates to bovine rennin and prorennin in the form of refractile bodies.

3 Claims, 1 Drawing Sheet

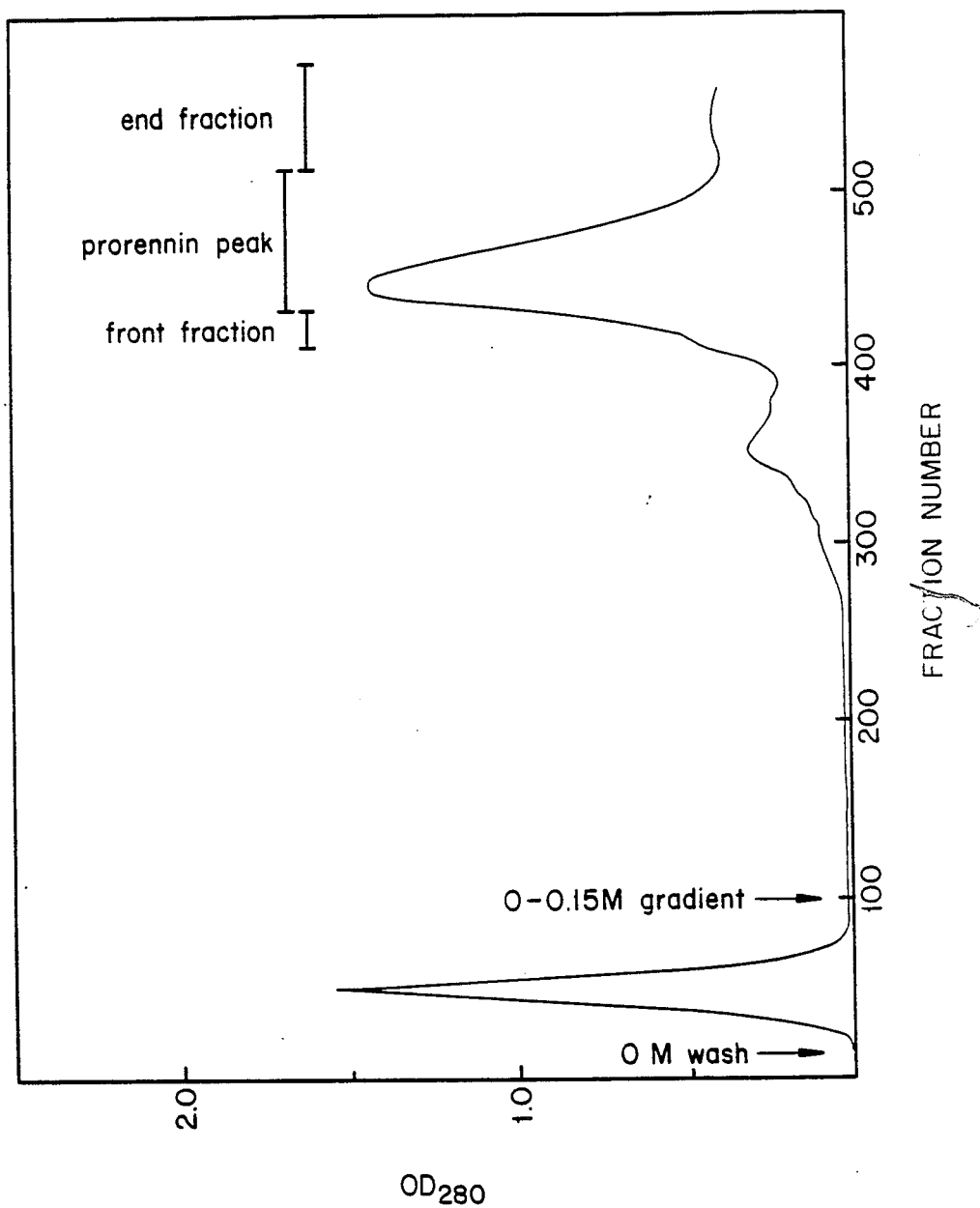

ISOLATION OF ACTIVE MICROBIALLY PRODUCED BOVINE RENNIN

This application is a continuation of application Ser. No. 452,251, filed Dec. 22, 1982, now abandoned.

Reference is made to U.S. Pat. Nos. 4,518,526; 4,511,502; 4,512,922; and 4,511,503 which claim the same priority date as the present application, Dec. 22, 1982. Reference is also made to Ser. No. 057,392 filed June 3, 1987; Ser. No. 927,778 filed Nov. 5, 1986, which also claim the priority date of the present application.

Reference is also made to U.S. Pat. Ser. No. 927,778 (pending) filed Nov. 5, 1986 which is a Continuation of U.S. Pat. Ser. No. 513,833 filed Jul. 14, 1983 (abandoned) which is a Continuation-In-Part of U.S. Pat. Ser. No. 452,227 filed Dec. 22, 1982 (abandoned).

Reference is also made to U.S. Pat. Ser. No. 057,392 filed Jun. 3, 1987 (pending), which is a Continuation of U.S. Pat. Ser. No. 855,827 filed Apr. 24, 1986 (abandoned) which is a Divisional of U.S. Pat. Ser. No. 513,883 filed Jul. 14, 1983 abandoned in favor of U.S. Pat. Ser. No. 927,778 filed Nov. 5, 1986 (which is a Continuation-In-Part of U.S. Pat. Ser. No. 452,227 filed Dec. 22, 1982 now abandoned).

BACKGROUND OF THE INVENTION

This invention relates to the recovery of active forms of proteins which are produced within microbial cultures through recombinant DNA techniques. More specifically, the invention concerns isolation of rennin or a precursor thereof, which is active in milk clotting or proteolysis, from proteins precipitated within bacterial cells as a result of expression of recombinant DNA.

The use of rennin in food processing where clotting of milk is a desirable step has been known for many centuries. Originally, in the process of making cheeses or other milk derived products, strips cut from the stomachs of domesticated young mammals were used as catalysts in the preparations. Later, extracts from, for example, calf stomach mucosa were substituted in cheese making and in preparation of puddings and the like. At the present time, calf stomach remains the major source of these materials, although the processes for extracting it have increased in sophistication.

Recently, it has been possible to prepare several known protein sequences using recombinant DNA techniques by transfecting microbes with gene sequences coding for the desired proteins. Rennin and its precursors are among these. See for example copending application U.S. Pat. Ser. No. 452,227, filed Dec. 22, 1982, now abandoned and British Patent Application GB 2,091,271 A, published 28 Jul. 1982. In the process described in the copending application, the desired rennin protein or its precursor is precipitated within the cell as a "refractile body". The present application describes a process for recovering active rennin activity from the refractile body protein produced in this way.

SUMMARY OF THE INVENTION

This invention relates to a process for recovering rennin capable of exhibiting milk-clotting activity from microbially produced rennin or its precursors which have been precipitated in the microbial host as refractile body proteins.

In another aspect, the invention relates to the rennin or its precursor so produced.

BRIEF DESCRIPTION OF THE DRAWINGS

FIG. 1 is the elution profile of microbially produced prorennin from DEAE cellulose.

DETAILED DESCRIPTION

A. Definitions

As used herein, "microbial rennet" refers to an enzyme preparation which is capable with or without conventional activation of forming a cheese curd in milk utilizing the mechanism of isolated calf rennin—i.e., cleaving the phenylalanine/methionine linkage in casein type proteins. The definition of "microbial rennet" thus includes proteins which are identical in amino acid sequence to calf rennin and its precursors, and those which are similar to it, though not identical, and which exhibit the same behavior. It includes any protein sequence which can be activated using conventional techniques to exhibit rennin activity. A classic example is that of prorennin, which is activated to rennin by treating the precursor prorennin at low pH. Preprorennin, which contains an additional 16 amino acids at its N terminus, may similarly be activated by incubating at low pH values. As above, proteins functionally similar to prorennin and preprorennin are also included.

The amino acid sequence of rennin and its natural, inactive precursor, prorennin, are known. Rennin has a molecular weight of approximately 35,000 and a sequence of 323 amino acids. Prorennin contains an additional 42 amino acids at the N-terminal end of the rennin molecule. Rennin itself, and therefore prorennin, exists naturally in two forms which differ only in the identity of the amino acid at position 286 of the prorennin molecule. In rennin A and corresponding prorennin, this amino acid is an aspartic acid residue, and in rennin B, and its corresponding prorennin, it is a glycine residue (Foltmann, B., et al., *Proc. Nat. Acad. Sci. (USA)*, 74:2321 (1977), and *J. Biol. Chem.*, 254:8447 (1979); both forms are active. An additional "preprorennin" precursor containing an additional 16 amino acids has also been disclosed (see GB 2, 091, 271, supra).

"Host cells" includes, where used in the context of a starting material in a procedure description for heterologous protein isolation, any of the forms in which the cells could be so used. It includes, for example, besides the harvested cell paste, the entire cell culture, a frozen sample of the paste, or a frozen and thawed sample of the paste. Thus the phase "treating host cells in a buffered solution" may refer, for example, to manipulation of the whole culture broth or to a preparation using spun down cells.

"Reactivation", as used herein, is almost synonymous with "refolding"—i.e., it refers to assurance of biological activity for protein preparation by placing it in a conformationally active form. "Reactivation" does not, as defined herein involve any change in the amino acid sequence and does not include, for example "activation" of the type wherein peptide precursors are cleaved to their active forms, such as conversion of trypsinogen to trypsin or prorennin to rennin.

"Ionic strength" refers to the conventional measure of ion concentration in aqueous solution. It is defined as ½ of the sum (over all ions in solution) of the product of the concentration of each ion, times the square of the charge thereon.

"Denaturing solution" refers to a solution which contains a "denaturant". "Denaturant", as used herein, refers to those chaotropic compounds or materials which, in aqueous solution and in suitable concentrations are capable of changing the spatial configuration or conformation of proteins through alternations at the surface thereof, either through altering, for example, the state of hydration, the solvent environment, or the solvent-surface interaction. Examples of such denaturants include urea, guanidine hydrochloride, sodium thiocyanate and detergents, such as SDS and Triton. It does not include such drastic and irreversible denaturing procedures as high temperature and high acidity.

It will be noted that some of the listed reagents are strong denaturants, while others are weaker, and that, of course, the concentration of any of these will directly affect its strength and effectiveness. There can be no specifically exact dividing line between "strong" and "weak", however, strong denaturing conditions more completely "unfold" the protein from whatever conformation it would spontaneously have preferred due to its amino acid sequence having conferred areas of hydrophilicity and hydrophobicity along the chain under physiological conditions. The most commonly used strongly denaturing environment useful in dissolving refractile protein is a fairly high (4–9M) concentration of the ionic denaturant, guanidine hydrochloride. Urea is the most frequently used example of a weak denaturant as even fairly high (e.g. 7M) concentrations permit the retention of some protein secondary structures, and provide a route to refolding to the "native" conformation. It happens also to be nonionic in character, which is significant with respect to its use in those aspects of the invention which entail the use of, for example, ion exchange techniques.

Accordingly, a "strongly denaturing" solution refers to a solution which will effectively "unfold" a protein also dissolved in the solution. The unfolding will be relatively extensive, but reversible. Solutes which are effective in carrying out unfolding to this extent are exemplified by guanidine hydrochloride and sodium thiocyanate, usually in relatively high concentrations in the range of approximately 4–9M, and detergents usually supplied in concentrations of the order of 0.01–2 percent.

"Weakly denaturing solutions" refers to those solutions which permit at least partial folding of a protein into the spatial conformation in which it finds itself when operating in its active form under endogenous or homologous physiological conditions, and also solubilizing any intermediate forms between the "denatured" form as would be found in a strongly denaturing solution, and the properly folded conformation. Examples of such weakly denaturing solutions are high concentrations of urea, ordinarily in the range of 4–9M and low concentrations of the denaturants set forth above which, in high concentrations, are strongly denaturing. These latter "low" concentrations are ordinarily in the range of 0.5 to approximately 2M. Occasionally, however, the functional status of "weakly denaturing solution" can also be observed simply under fairly standard enzyme assay conditions such as, for example, low buffer concentrations of the order of 0.1M and below, and physiological pH. As used in this invention, "weakly denaturing solution" refers to the functional definition—i.e. those solutions which permit refolding from whatever contorted conformation the protein has, for whatever reason, assumed through intermediates soluble in this solution, to a conformation which is capable of exhibiting biological activity.

"Active" microbial rennet refers to a protein which exhibits proteolytic activity qualitatively identical to that of calf rennin or its precursors (see "microbial rennet" supra).

B. General Procedure

Microbial rennet is prepared in refractile form in bacterial hosts by the methods described in copending Genentech application docket no. 100/147. In general, expression vectors containing the sequence encoding calf rennin, prorennin, or other suitable precursor, are prepared using recombinant techniques, and transfected into a microbial host culture, most conveniently a bacterial host, and preferably E. coli. The host cells are grown under conditions which are favorable to the expression of the desired rennet protein, and the refractile bodies formed isolated according to the method of the invention.

In this method, the cells are suspended in aqueous buffer comprising either the culture medium itself or a buffered solution of suitable ionic strength. Typical ionic strengths which are useful in the method of the invention are in the range of 0.01M to 2M ionic strength. Suitable pH ranges are 5–9, preferably about 6–8. The suspended cells are disrupted by any convenient means, such as mechanical methods, for example, Manton Gaulin press, a French press, or sonication; or enzymatic or chemical means, such as, for example lysozyme. After the cells are disrupted, the suspension is centrifuged at low speeds from about 500× g to about 5,000× g, preferably around 1,000× g in a standard centrifuge, for 10 minutes to 2 hours, preferably around ½ hour. The pellet contains the desired protein, and may be washed by conventional techniques if desired.

The pellet is dissolved in a strongly denaturing solution at approximately neutral pH, from about pH 5 to about pH 9, preferably around pH 7–8. Preferable strongly denaturing solutions are 4–9M, preferably 5–6M guanidine hydrochloride.

Optionally, further purification techniques may be used, such as ion exchange chromatography or treatment with molecular sieve or other gel permeation techniques.

The solution is then treated with a system containing a sulfhydryl compound (RSH) and its corresponding disulfide (RSSR), for example β-mercaptoethanol, reduced glutathione, cysteamine, or cysteine and the corresponding oxidized forms, preferably gultathione in the reduced (GSH) and the oxidized (GSSG) forms. The pH is adjusted to a value such that the sulfhydryl compound (RSH) is at least partially in ionized form (RS-) so that nucleophilic displacement of the sulfonate is enhanced. Alternatively the reduced form alone in the presence of air may be used, as sufficient disulfide will be generated in this environment. Typically, the RSH to RSSR molar ratio is approximately between 20 to 1 and 5 to 1, preferably around 10 to 1, and the total glutathione or other reagent concentration in a 0.05 to 5 mM range. The mixture is incubated at about 0° C. to 37° C., preferably around room temperature, for 4 to 24 hours, preferably overnight.

The resulting protein solution can then, of course, optionally be subjected to further purification using standard techniques at this point as well; if the presence of any remaining concentration of denaturant is objectionable, buffer exchange into the desired conditions may also be performed.

C. Examples

The following examples are intended to illustrate, but not limit the invention.

PREPARATION A

Production of Cells Containing Prorennin Refractile Bodies

*E. coli* K12 (W3110/pR1AX), a bacterial strain expressing the coding sequence for calf prorennin such that the amino acid sequence is produced in the form of refractile bodies, was prepared and grown as described in copending U.S. Pat. Ser. No. 452,227 filed Dec. 22, 1982. Briefly, the cells were grown in a broth containing 10 g/l yeast extract and 5 g/l tryptone to a cell density of about $2-4 \times 10^8$ cells/ml. 3-5 percent of the volume of this culture is then inoculated into M9 medium (J. H. Miller, *Experiments in Molecular Genetics*, p. 434, Cold Spring Harbor Laboratory, 1972) or other similar mineral salts medium containing 40-120 mg/l tryptophan. The cultures, grown in a bench fermenter with sufficient agitation and aeration to achieve a growth rate of 60-90 minutes/cell division, were fed glucose to maintain growth and the pH maintained at 6.8-7.2. At a cell density of 5 to 10 grams dry weight/liter, indole acrylic acid (IAA) or indole propionic acid (IPA) was added to the cultures to a concentration of 25 to 50 mg/l. Two to five hours after the addition of IAA or IPA, the *E. coli* cells became elongated, and one or more refractile bodies per cell could be seen under phase contrast microscope at 1,000 fold magnification.

(The cells were then, optionally, killed by treating the medium with 0.25 percent phenol and 0.25 percent toluene for about ½ hour at room temperature. This kill step is not necessary to the method of the invention, and is utilized, in part, in order to comply with safety regulations governing the handling of recombinant DNA cells. The culture was then spun down, and the cell paste recovered.)

EXAMPLE 1

Recovery of Refractile Protein 346 g wet weight of the foregoing cells were suspended in 2.5 l of 50 mM Tris-HCl, pH 7.5, with 5 mM EDTA using a Tekmar homogenizer. The suspension was passed through a Manton Gaulin press 4 times at 6,000 psi with cooling. The refractile bodies were then harvested by spinning at $1,000 \times$ g for 45 minutes with a GS-3 rotor in a Sorvall RC-5B centrifuge, resuspended in 300 ml of the same buffer plus 6.0 g of lysozyme, and pelleted again by centrifuging at $1,000 \times$ g in an SS-34 rotor for 12 minutes. The pellet was again resuspended in 150 ml of the same buffer, and pelleted in the SS-34 rotor as above. The pellet was stored with 0.01 percent sodium azide in a total volume of 150 ml of the same buffer. Aliquots of this material were taken as needed.

EXAMPLE 2

Reactivation of Refractile Protein

An aliquot of the refractile body material, prepared as in Example 1, containing 10 mg of protein was pelleted in a microfuge, and resuspended in 1 ml of 6M guanidine HCl and 50 mM Tris-HCl, pH 8.0. To this solution was added 100 l of a solution containing 100 mg/ml ad 10 mg/ml sodium sulfite and sodium tetrathionate, respectively. The resulting solution was allowed to stand overnight at room temperature, and then dialyzed against 50 mM Tris-HCl, pH 8.0, 5M urea overnight at 4° C. 10 l of a solution 100 mM in reduced glutathione and 10 mM in oxidized glutathione was then added. The solution was allowed to stand for 18 hours at 4° C., and the urea removed by dialysis vs. the buffer containing Tris-HCl, pH 8.0 and 1 mM reduced glutathione.

An aliquot of the resulting solution was dialyzed against a large excess of 0.01N NCl at 4° C. and incubated for 2 hours at 37° C. to convert the prorennin contained therein to the active rennin form. 90-l of this solution was then mixed with 10 l of 1M Tris-HCl pH 8.0 to neutralize the acid.

The solution was assayed for rennin activity according to the method of Sokol et al., *J. Clin. Microbiol.*, 9:538 (1979) except that Difco brain heart infusion was omitted from the plates. Briefly, the assay comprises measuring the diameter of coagulation zones on skim milk plates and correlating these values to an electrophoretically homogenous rennin standard.

The results of this assay are shown in Table 1.

TABLE 1

Milk Coagulation Activity of Rennin and Refolded, Activated Refractile Bodies on Skim Milk Plates: Effect of Anti-Rennin and Control Antibodies on Activity.

|  | Diameter of Coagulation Zone* | | |
|---|---|---|---|
| Control Purified Activated Prorennin | 2.0 g | 0.2 g | 0.02 g |
| No additions | 22 | 18 | 13 |
| Plus 16 g of purified control antibody** | 22 | 17 | 11 |
| With 16 g of purified anti-rennin antibody | 20 | 15 | 0 |
| Activated Microbial Prorennin | 18 g | 1.8 g | 0.18 g |
| No additions | 16.5 | 11 | Faint Spot |
| Plus 16 g of purified control** antibody | 12 | 9 | 0 |
| Plus 16 g of purified anti-rennin antibody | 10 | 0 | 0 |

*Diameters are in mm.
**Purified anti-human-FIF was used as a control antibody.

As seen in Table 1, approximately the same activity as judged by diameter of coagulation is given by 0.4 g of control prorennin as is given by 18 g of the microbial preparation. The behavior of both with respect to inactivation with anti-rennin antibody is similar. (Control antibody is partially successful in inactivation, but the effectiveness of anti-rennin antibody is impaired by the activity of the rennin itself.)

EXAMPLE 3

Purification of Prorennin 432 g wet weight of cells prepared as described in Preparation A were suspended in a total volume of 3 l, 50 mM Tris-HCl, pH 7.5, 5 mM EDTA, and 6 g lysozyme using a Tekmar homogenizer, and passed through a Manton Gaulin press at 6,000 psi. The refractile bodies were pelleted at $4,000 \times$ g for 30 minutes in a GS-3 rotor, and the pellet resuspended in 2 l of 50 mM HCl, pH 7.5, 5 mM EDTA, and repelleted as described above. The pellet was dissolved in 632 ml of 6M guanidine-HCl and 50 mM Tris, pH 8.0, using the Tekmar, and the suspension centrifuged at $5,000 \times$ g for 10 minutes in a GSA rotor. To the dissolved protein was added 63.2 mls of 200 mg/ml sodium sulfite and 100 mg/ml sodium tetrathionate, and the solution was incubated 4 hours at room temperature. The sulfonating agents and guanidine HCl were then removed by diafiltration into 5M urea, 50 mM Tris-HCl, pH 7.5, with monitoring by pH and conductivity of the solution.

The diafiltered material was loaded onto a 10×33 cm DE-52 column equilibrated with 50 mM Tris-HCl, pH 7.5, 5M urea. The column was washed with 3.5 l of the same buffer at a flow rate of 500 ml/hr., and the prorennin eluted with a linear 0 to 0.15M sodium chloride gradient in the foregoing buffer at a flowrate of 1 l/hr. The purity of fractions was determined by electrophoresis and the fractions of highest purity pooled to give a total volume of 1800 ml. The profile of the elution pattern is given in FIG. 1. The fractions indicated as prorennin peak represent the 1800 ml pool.

The prorennin peak was refolded by diafiltering the sulfonated protein into a buffer solution consisting of 50 mM Tris HCl, pH 8.5, 5M urea. To this solution was added sufficient solid oxidized and reduced glutathione to achieve a final concentration of 0.1 mM and 1.0 mM respectively, and the reaction allowed to proceed overnight at 4° C. The resulting solution was dialyzed against 3 changes of 37.5 l per change of 50 mM Tris-HCl, pH 8.0, 0.1 mM reduced glutathione.

The lyzate was then concentrated 4 times to 500 ml and contained 11 mg/ml or 5.5 g total protein as determined by biuret.

EXAMPLE 4

Milk Clotting Activity of Purified Prorennin Derived Enzyme

A. Skim Milk 5 ml aliquots of the prorennin dialysate concentrate prepared in Example 3 were activated by adding 0.5 ml of 0.45N HCl to give a pH of approximately 2, and incubating for 1 hour at 30° C. Skim milk was prepared by adding 1 g of dry milk (milk powder skim, U.S. Biochemical Corp, NDC12894) into 10 ml of 100 mM.

NaOAc, pH 6.0, 10 mM $CaCl_2$, and homogenizing 50 times. The milk was preincubated at 30° C.

Enzyme samples were prepared as follows:

5 l and 10 l of active prorennin were added to 95 l and 90 l respectively of 100 mM sodium acetate, pH 6.0, 10 mM $CaCl_2$, and preincubated at 30° C.

A 1:30 dilution of Marshall rennet (Miles laboratories) was also prepared as a control.

100 l of each enzyme preparation was added to a 900 l aliquot of skim milk at 30° C., and clotting time recorded. Units of enzyme activity were calculated using the equation: 198/(sec-8)×dilution factor=units per ml of undiluted enzyme i.e., the original dialyzate or the undiluted rennet. The sample containing 5 l of activated prorennin gave 202.6 units per ml of original dialysate, that containing 10 l of prorennin gave 380.8 units per ml and that of the control gave 1563 units per ml of undiluted Rennet (compared to the label value of 1600 unit/ml). A subsuquent 1:20 dilution of the enzyme was also tested, and confirmed a value of the prorennin preparation at 374 units per ml of the dialysate.

B. Pasteurized Milk

The procedure is similar to that in paragraph A. The dialysate containing prorennin prepared in Example 3 was activated by mixing 19.6 ml of 0.45N HCl with 196 ml of dialysate, to give pH 2 and incubating at 30° for 45 minutes.

To test clotting, to two 10 ml portions of pasteurized milk were added respectively, 1.98 l of undiluted Marshall rennet and 8.5 l of the dialysate. The respective clotting times were 18 min. and 9 min.

EXAMPLE 5

Preparation of Cheese 5 batches, of 7,000 g each of milk containing 3.95 percent fat and 12.57 percent solids were preincubated, each with 16 g of D-gluconic acid lactone for 30 minutes at 30° C. 2.5 ml of activated microbial prorennin as prepared above were added to batches 3, 4, and 5, and sufficient Marshall rennet was added to batches 1 and 2 that the milk the coagulated in approximately 25 minutes added. After 25 minutes, the curd was cut, heated to 102° F. over 15 minutes, drained of whey, pressed and weighed.

The results of this clotting assay are shown in the table below:

| Batch No. | percent yield (g dry matter 100 g milk) | percent curd (corrected for std moisture) | actual percent yield of wet curd |
|---|---|---|---|
| 1 | 6.76 | 11.08 | 11.92 |
| 2 | 6.72 | 11.02 | 11.85 |
| 3 | 6.82 | 11.18 | 12.05 |
| 4 | 6.95 | 11.39 | 11.95 |
| 5 | 6.70 | 10.98 | 11.52 |

In the above table, yields are given in the following terms: Column 1 give percent yield of dry matter with respect to whole milk. Column 2 is calculated by dividing the values in Column 1 by 0.61; it gives the percent yield as wet weight that would be expected if the "usual" amount of moisture is present. Column 3 gives the percent wet weight actually obtained.

Of course, the wet weight yield of cheese will greater the higher the moisture content of the resulting cheese. Typically, cheese made in a process of this kind by rennet coagulation will contain a moisture content of approximately 39 percent. Accordingly, in column 2 the percentage of wet weight is calculated assuming a 39 percent moisture content in the produce. This allows comparison with yields obtained in commercial processes wherein these moisture contents are obtained. Typically, cheddar cheese prepared from 3.5 percent fat milk containing a moisture of 39 percent will give a wet yield of 9.7 percent. All of the samples in the above trial contained approximately 11 percent yield, which is significantly higher than that ordinarily obtained due to the higher fat content of the milk. As seen above, the commercial rennet and the microbially produced activated rennin gave comparable yields, but the yield for the commercially produced rennet was slightly lower than the yield in batch 3. (The yields obtained in batches 4 and 5 are not really comparable as the clotting time was appreciably less than ideal in these trials.) Also, the moisture of the cheese produced was somewhat higher than the 39 percent typically obtained, ranging from approximately 43 to 44 percent in the first three batches to approximately 42 percent in batches 4 and 5.

While the yields as determined by batch 3 are not greatly higher than those in the controls, it appears that some improvement may have been effected. It is to be noted in this regard, that even slight increases in yield are regarded as significant. This is because of the large scale involved in commercial processes where only a small improvement results in a large economic benefit. For example, in a paper entitled "Effect of Milk Clotting Enzymes on Cheese Yield" presented at the Cheese Industry Conference in Logan, Utah on Sept. 1, 1982 by Dr. Robert L. Sellers, it is pointed out that differences of even hundreths of a percentage point are significant. For example, wet weight yields of 9.947 percent were compared favorably with yields 9.909 percent for various commercial rennet products.

EXAMPLE 6

Manufacture of Cheese Using Microbial Rennin

Milk 3.95 percent in fat produced at the University of Kentucky Dairy was pasteurized at 145° F. for 30 minutes and then cooled to 36° F. for overnight storage. The milk was then warmed to 85° F. and placed in vats in lots of 400 lbs. per vat.

4 g Chris Hansen culture CH60 was added to each vat, and the mixture allowed to stand at 86° F. for one hour. Calf rennin as prepared in Example 3, was then added over a period of 25–30 minutes to batches 2 and 3 and Marshall rennet was added to batch 1. During this time, curd was formed which was cut at the end of the 30 minutes with 3⅛" knives, and then allowed to heal for 15 minutes. The curd temperature was then increased to 102° F. over a 30 minute period and maintained at that temperature, with agitation until the pH reached 6.1.

Whey was then drained, and the curd allowed to mat with turning every 10–15 minutes. When pH of 5.8 was reached, the curd was stacked two high, and at pH 5.6 it was stacked three high. When the pH reached 5.4, the curd was mulled, salted, hooped, and pressed.

After a 30 minute pressing, hoops were dressed and pressed for an additional 16 hours, and the cheese packaged in a cryovac saran bag, S-11 which was then heat shrunk in boiling water. The bagged cheese was then stored in a 40° cooler.

The results are shown in the following table:

| Batch | Amt added | Clotting time | Percent dry wt. yield (g dry matter/ 100 g milk) | Percent wet wt. curd corrected for std moisture | Actual percent yield of wet curd | Grade |
| --- | --- | --- | --- | --- | --- | --- |
| 1 | 40 ml | 25 min | 6.72 | 11.02 | 10.94 | 11/15 |
| 2 | 84 ml | 23 min | 7.00 | 11.46 | 11.44 | 13/15 |
| 3 | 90 ml | 11 min | 6.71 | 10.99 | 11.00 | 12/15 |

As the table shows, reasonable clotting times were given only batches 1 and 2. Again the yield, whether based on a standard 39 percent moisture content, or on the actual amount of moisture, was higher in the case of the microbially prepared, activated, prorennin. In any case, comparable yields were obtained. Perhaps more important, are the results of the tests on the quality of the cheese produced. These are expressed as "grade" in the table, wherein the evaluation on a scale of 15 as judged by two experienced cheese tasters is tabulated. The scale is structured on a standard set of criteria including taste, texture, color, and aroma which is promulgated by the USDA and in common use in the industry. As the table shows, the highest quality cheese of the three batches was batch number 2 prepared with the proper clotting time using the microbial rennet. That cheese, while somewhat pasty, was graded higher than the products of batches of 1 and 3.

It may further be remarked that in all three batches, the assay with respect to bacteria counts was entirely analogous. In the pasteurized milk before treating with starter, the "plate count agar" test which is designed to count total bacteria, yielded in the range of 1-½ to $3 \times 10^2$ total bacteria, while the violet red bile medium, designed to detect coliform gave less than 10 microorganisms per ml of milk. After starter is added, of course, the total count increase as this constitutes an addition of bacteria to aid in ripening these resulting cheese. In all three batches, total bacterial counts as measured on "all purpose Tween" medium and "Ellikers" medium were in the range of 1 to $2 \times 10^7$ cells per ml. Approximately 4 to $6 \times 10^5$ total bacteria per ml remain in the whey after the curd had been separated in all cases whether assayed by "all purpose Tween" or Ellikers. Again, the coliform count in all cases was less than ten cells per ml.

In summary, the results of cheese production on a commercial scale-i.e. 400 lb. lots, is comparable with, if not superior to, commercial calf rennet for microbially produced activated prorennin.

We claim:

1. Isolated bovine rennin or prorennin in the form of a refractile body.

2. Isolated bovine rennin according to claim 1.

3. Isolated bovine prorennin according to claim 1.

* * * * *

UNITED STATES PATENT AND TRADEMARK OFFICE
CERTIFICATE OF CORRECTION

PATENT NO. : 4,935,369

DATED : June 19, 1990

INVENTOR(S) : Hayenga, et al.

Page 1 of 2

It is certified that error appears in the above-identified patent and that said Letters Patent is hereby corrected as shown below:

Column 4, line 39, following "5-6M guanidine hydrochloride" insert

--The solubilized protein is then subjected to sulfitolysis by treating with a suitable concentration of sulfite 10N, in the range of 5-200 mg/ml, preferably around 15-30 mg/ml as calculated for sodium sulfite, or corresponding molar amounts of other sulfite salts, and a mild oxidizing agent sufficient to regenerate disulfide from any sulfhydryl groups which result from the reaction. Suitable oxidizing agents are, for example, metal cations and sodium tetrathionate, preferably sodium tetrathionate. Sodium tetrathionate is added in the amount of approximately 1-20 mg/ml, preferably around 10 mg/ml though corresponding molar amounts of other agents may be used. The solution is then allowed to stand 4-24 hours, preferably overnight at $15^{\circ}C$ to $35^{\circ}C$, preferably around room temperature.

The reaction is then terminated by removal of the reagents, preferably through dialysis into a weakly denaturing solution, such as 1-9 M urea or a diluted concentration such as 0.5-2 M guanidine hydrochloride, preferably around 5 M urea.

It is believed that the mechanism of this reaction involves a nucleophilic attack by the sulfite ion to break the disulfide bond. In any event, the resulting linkage is a protein-S-$SO_3$, i.e., a protein-S-sulfonate.

UNITED STATES PATENT AND TRADEMARK OFFICE
CERTIFICATE OF CORRECTION

PATENT NO. : 4,935,369

DATED : June 19, 1990

INVENTOR(S) : Hayenga, et al

It is certified that error appears in the above-identified patent and that said Letters Patent is hereby corrected as shown below:

When the sulfonated protein is placed into the weakly denaturing medium, this medium provides a route to proper refolding, the protein no longer being trapped by the incorrect disulfide linkages. If urea is used as a weakly denaturing solution, appropriate concentrations are 1-9 M preferably around 5 M. The pH is kept at approximately 5-9, preferably around 6-8 with suitable buffer, and optionally with added EDTA or other chelating agent. If dilution is used, appropriate concentrations are about 0.5 M to 2 M in the original strong denaturant.--

Signed and Sealed this

Seventh Day of April, 1992

Attest:

HARRY F. MANBECK, JR.

*Attesting Officer*     *Commissioner of Patents and Trademarks*